(12) United States Patent
Balgobin et al.

(10) Patent No.: US 7,708,754 B2
(45) Date of Patent: *May 4, 2010

(54) STRETCH RESISTANT EMBOLIC COIL DELIVERY SYSTEM WITH MECHANICAL RELEASE MECHANISM

(75) Inventors: Keith Balgobin, Pembroke Pines, FL (US); Vladimir Mitelberg, Austin, TX (US); John H. Thinnes, Jr., Miami Beach, FL (US)

(73) Assignee: Codman & Shurtleff, PC, Raynham, MA (US)

( * ) Notice: Subject to any disclaimer, the term of this patent is extended or adjusted under 35 U.S.C. 154(b) by 173 days.

This patent is subject to a terminal disclaimer.

(21) Appl. No.: 11/755,364

(22) Filed: May 30, 2007

(65) Prior Publication Data

US 2008/0045997 A1     Feb. 21, 2008

Related U.S. Application Data

(63) Continuation-in-part of application No. 11/302,730, filed on Dec. 14, 2005, now abandoned, which is a continuation-in-part of application No. 11/143,052, filed on Jun. 2, 2005, now Pat. No. 7,371,251.

(51) Int. Cl.
*A61M 29/00* (2006.01)
*A61F 2/06* (2006.01)
(52) U.S. Cl. .................. 606/200; 606/191; 623/1.11
(58) Field of Classification Search ........... 606/142, 606/151, 191, 200, 213; 623/1.1, 1.11
See application file for complete search history.

(56) References Cited

U.S. PATENT DOCUMENTS 5,108,407 A    4/1992   Geremia et al.

(Continued)

FOREIGN PATENT DOCUMENTS

EP           754435 A1      1/1997

(Continued)

OTHER PUBLICATIONS

European Search Report EP 06 25 2708 dated Sep. 11, 2006 with Annex to the European Search Report.

(Continued)

*Primary Examiner*—Julian W Woo
*Assistant Examiner*—Melissa Ryckman
(74) *Attorney, Agent, or Firm*—Cook Alex Ltd.

(57) ABSTRACT

A medical device for placing an embolic device at a predetermined site within a vessel of the body including a delivery catheter and a flexible pusher member slidably disposed within the lumen of the catheter. An embolic device is retained within the delivery catheter by a mechanical interlocking mechanism which includes an engagement member attached to the distal end of the pusher member and extends through a retaining ring at the proximal end of the embolic device. A detachment member extends through an aperture at the distal end of the engagement member thereby locking the embolic device onto the pusher member. A kicker member extends from the distal end of the pusher member and is comprised of a shape memory material adapted to lift the retaining ring off of the engagement member at human body temperature when the detachment member is withdrawn from the aperture of the engagement member.

20 Claims, 10 Drawing Sheets

U.S. PATENT DOCUMENTS

| | | | |
|---|---|---|---|
| 5,122,136 A | 6/1992 | Gugliemi et al. | |
| 5,250,071 A | 10/1993 | Palermo | |
| 5,263,964 A | 11/1993 | Purdy | |
| 5,334,210 A | 8/1994 | Gianturco | |
| 5,350,397 A | 9/1994 | Palermo et al. | |
| 5,382,259 A | 1/1995 | Phelps et al. | |
| 5,540,680 A | 7/1996 | Gugliemi et al. | |
| 5,582,619 A | 12/1996 | Ken | |
| 5,601,600 A | 2/1997 | Ton | |
| 5,800,455 A | 9/1998 | Palermo et al. | |
| 5,853,418 A | 12/1998 | Ken et al. | |
| 5,895,391 A | 4/1999 | Farnholtz | |
| 5,895,411 A | 4/1999 | Irie | |
| 5,925,059 A * | 7/1999 | Palermo et al. | 606/191 |
| 6,113,622 A | 9/2000 | Hieshima | |
| 6,193,728 B1 | 2/2001 | Ken et al. | |
| 6,203,547 B1 | 3/2001 | Nguyen et al. | |
| 6,238,415 B1 | 5/2001 | Sepetka et al. | |
| 6,361,547 B1 | 3/2002 | Hieshima | |
| 6,500,149 B2 | 12/2002 | Gandhi et al. | |
| 6,537,314 B2 | 3/2003 | Langberg et al. | |
| 6,544,225 B1 | 4/2003 | Lulo et al. | |
| 6,554,849 B1 | 4/2003 | Jones et al. | |
| 6,607,538 B1 | 8/2003 | Ferrera et al. | |
| 6,660,020 B2 | 12/2003 | Wallace et al. | |
| 6,689,141 B2 | 2/2004 | Ferrera et al. | |
| 6,793,673 B2 | 9/2004 | Kowalsky et al. | |
| 6,811,561 B2 | 11/2004 | Diaz et al. | |
| 6,835,185 B2 | 12/2004 | Ramzipoor | |
| 6,849,303 B2 | 2/2005 | Dave | |
| 6,902,572 B2 | 6/2005 | Beulke | |
| 6,958,068 B2 | 10/2005 | Hieshima | |
| 6,966,914 B2 | 11/2005 | Abe | |
| 6,994,711 B2 | 2/2006 | Hieshima et al. | |
| 7,367,987 B2 * | 5/2008 | Balgobin et al. | 606/200 |
| 7,371,251 B2 * | 5/2008 | Mitelberg et al. | 606/200 |
| 7,371,252 B2 * | 5/2008 | Balgobin et al. | 606/200 |
| 7,377,932 B2 | 5/2008 | Mitelberg | |
| 2001/0002438 A1 | 5/2001 | Sepetka et al. | |
| 2002/0111647 A1 | 8/2002 | Khairkhahan et al. | |
| 2002/0165569 A1 | 11/2002 | Ramzipoor et al. | |
| 2004/0034363 A1 | 2/2004 | Wilson et al. | |
| 2004/0044361 A1 | 3/2004 | Frazier et al. | |
| 2004/0111095 A1 | 6/2004 | Gordon et al. | |
| 2005/0043755 A1 | 2/2005 | Wilson et al. | |
| 2005/0113864 A1 | 5/2005 | Gandhi et al. | |
| 2006/0276823 A1 | 12/2006 | Mitelberg et al. | |
| 2006/0276824 A1 * | 12/2006 | Mitelberg et al. | 606/200 |
| 2006/0276825 A1 * | 12/2006 | Mitelberg et al. | 606/200 |
| 2006/0276826 A1 * | 12/2006 | Mitelberg et al. | 606/200 |
| 2006/0276827 A1 * | 12/2006 | Mitelberg et al. | 606/200 |
| 2006/0276828 A1 * | 12/2006 | Balgobin et al. | 606/200 |
| 2006/0276829 A1 | 12/2006 | Balgobin et al. | |
| 2006/0276830 A1 * | 12/2006 | Balgobin et al. | 606/200 |
| 2006/0276832 A1 * | 12/2006 | Balgobin et al. | 606/200 |
| 2006/0276833 A1 | 12/2006 | Balgobin et al. | |
| 2006/0276834 A1 * | 12/2006 | Balgobin et al. | 606/200 |
| 2007/0010849 A1 | 1/2007 | Balgobin et al. | |
| 2007/0010850 A1 | 1/2007 | Balgobin et al. | |
| 2007/0118172 A1 | 5/2007 | Balgobin | |

FOREIGN PATENT DOCUMENTS

| | | |
|---|---|---|
| EP | 832607 A1 | 4/1998 |
| EP | 832607 B1 | 8/2000 |
| EP | 754435 B1 | 12/2003 |
| WO | WO/96/38092 | 12/1996 |
| WO | WO 2004/008974 | 1/2004 |

OTHER PUBLICATIONS

European Search Report EP 06 25 6285 dated Feb. 26, 2007 with Annex to European Search Report.

* cited by examiner

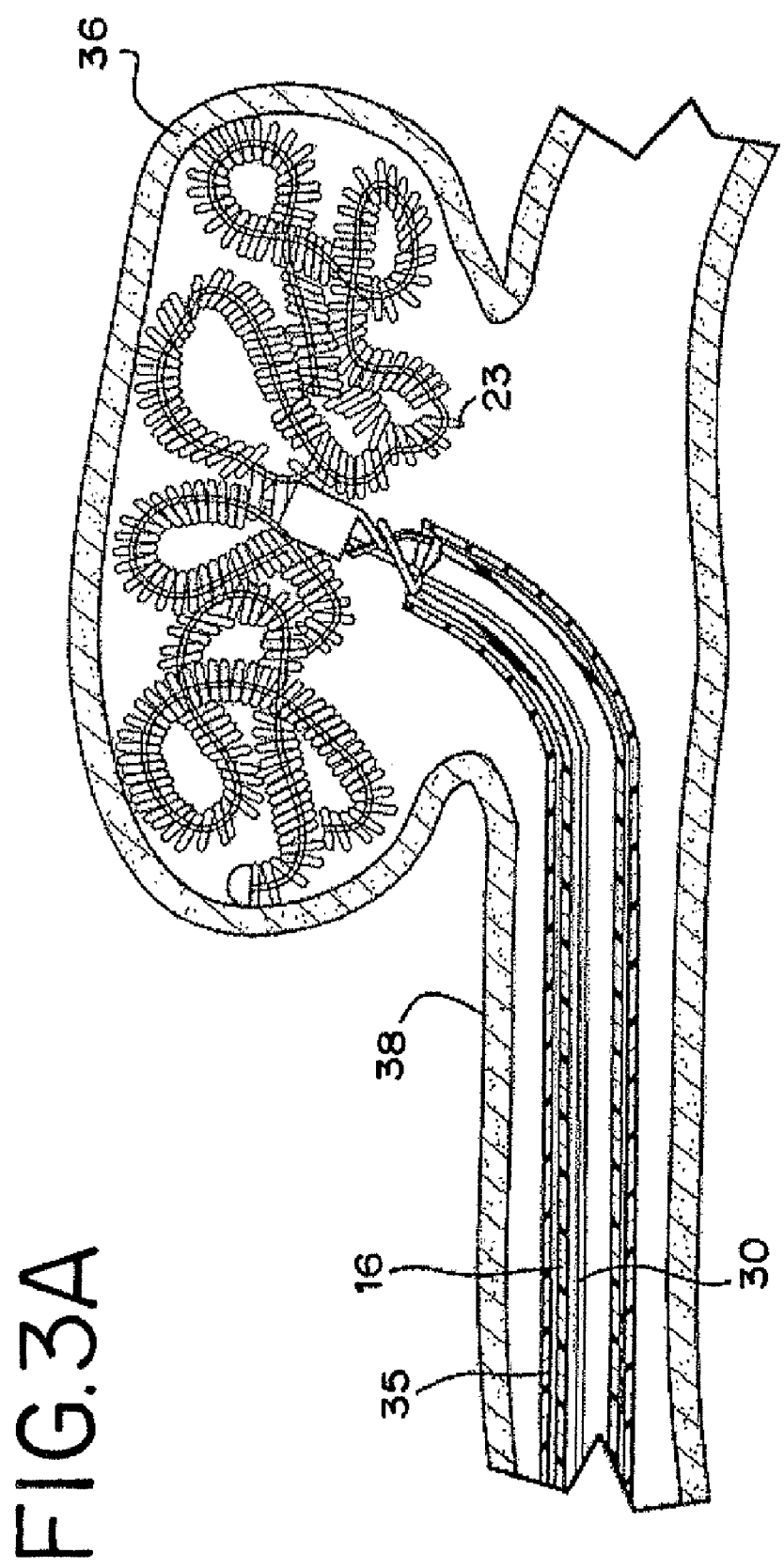

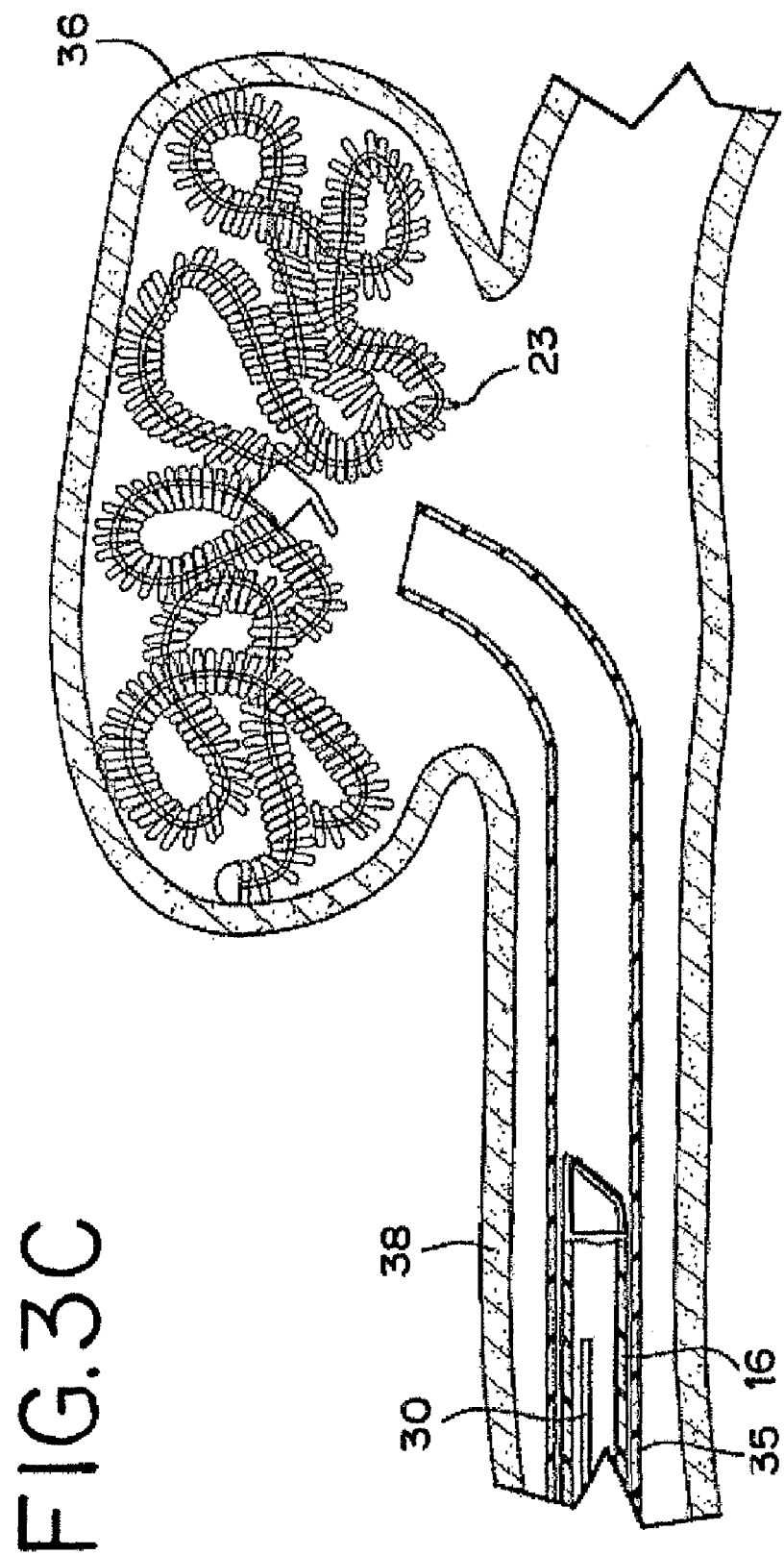

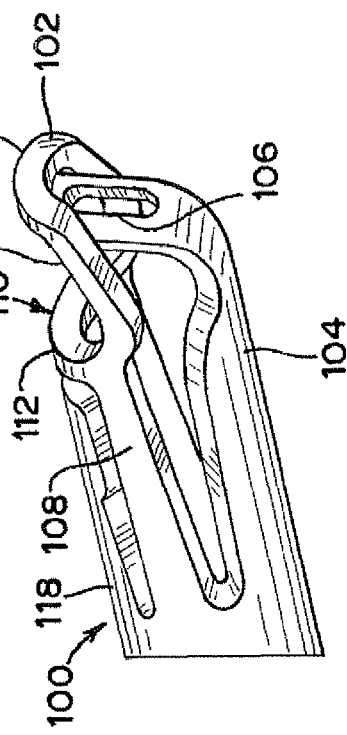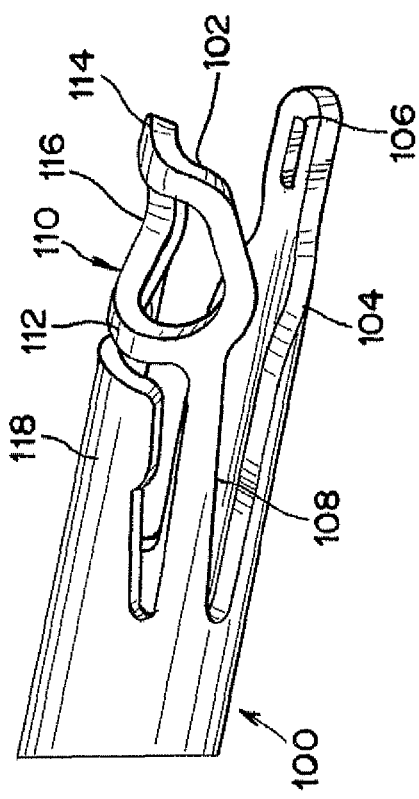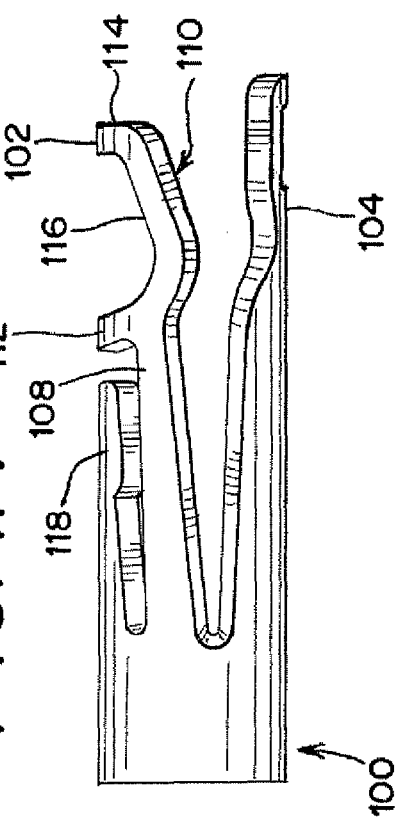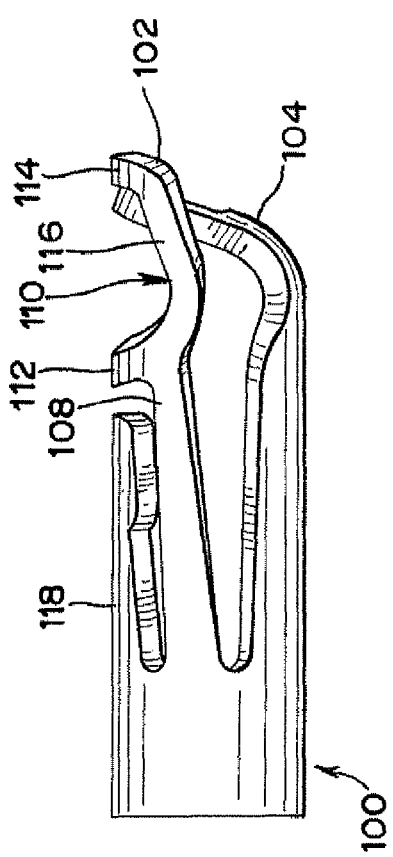

STRETCH RESISTANT EMBOLIC COIL DELIVERY SYSTEM WITH MECHANICAL RELEASE MECHANISM

CROSS-REFERENCE TO RELATED APPLICATIONS

This patent application is a continuation-in-part of U.S. patent application Ser. No. 11/302,730, filed on Dec. 14, 2005, entitled, "Stretch Resistant Embolic Coil Delivery System With Mechanical Release Mechanism," which is a continuation-in-part of U.S. patent application Ser. No. 11/143,052, filed on Jun. 2, 2005, entitled, "Stretch Resistant Embolic Coil Delivery System With Mechanical Release Mechanism."

BACKGROUND OF INVENTION

1. Field of the Invention

The present invention relates to a medical device for placing a stretch resistant embolic device at a predetermined site within a vessel of the human body, and more particularly, relates to a catheter-based deployment system for delivering an embolic device. This device is particularly suited to transport an embolic device, such as a stretch resistant embolic coil, through the tortuous vasculature of the human brain to a selected site within the vessel or within an aneurysm.

2. Description of the Prior Art

For many years, flexible catheters have been used to place various devices within the vessels of the human body. Such devices include dilation balloons, radiopaque fluids, liquid medications, and various types of occlusion devices such as balloons and embolic coils. Examples of such catheter-based devices are disclosed in U.S. Pat. No. 5,108,407, entitled, "Method and Apparatus for Placement of an Embolic Coil" and U.S. Pat. No. 5,122,136, entitled, "Endovascular Electrolytically Detachable Guidewire Tip for the Electroformation of Thrombus In Arteries, Veins, Aneurysms, Vascular Malformations and Arteriovenous Fistulas." These patents and the other patents and patent applications referenced herein are hereby incorporated herein by reference. These patents disclose catheter-based devices for delivering embolic coils to preselected positions within vessels of the human body in order to treat aneurysms, or alternatively, to occlude blood vessels at a particular location.

Coils which are placed in vessels may take the form of helically wound coils, or alternatively, may take the form of randomly wound coils, coils wound within coils or other such coil configurations. Examples of various coil configurations are disclosed in U.S. Pat. No. 5,334,210, entitled, "Vascular Occlusion Assembly" and U.S. Pat. No. 5,382,259 entitled, "Vasoocclusion Coil with Attached Tubular Woven or Braided Fibrous Covering." Embolic coils are generally formed of a radiopaque metallic material, such as platinum, gold, tungsten, or alloys of these metals. Often, several coils are placed at a given location to occlude the flow of blood through the vessel, or aneurysm, by promoting thrombus formation at the particular site.

In the past, embolic coils have been placed within the distal end of a catheter. When the distal end of the catheter is properly positioned, the coil may then be pushed out of the end of the catheter with a pusher member to release the coil at the desired location. This procedure for placement of an embolic coil is conducted under fluoroscopic visualization such that the movement of the coil through the vasculature of the body may be monitored and the coil placed at the desired location.

Another procedure involves the use of glue or solder for attaching the coil to a guidewire, which in turn, is placed within a flexible catheter for positioning the coil within the vessel at a preselected position. Once the coil is in the desired position, the coil is held in position by the catheter and the guidewire is pulled proximally to thereby cause the coil to become detached from the guidewire and released from the catheter. Such a coil positioning system is disclosed in U.S. Pat. No. 5,263,964 entitled, "Coaxial Traction Detachment Apparatus and Method."

Still another coil positioning procedure is that of having a catheter with a socket at the distal end of the catheter for retaining a ball which is, in turn, bonded to the proximal end of the coil. The ball, which is generally larger in diameter than the outside diameter of the coil, is placed in the socket within the lumen at the distal end of the catheter and the catheter is then moved into a vessel in order to place the coil at a desired position. Once the position is reached, a pusher wire with a piston at the end thereof is pushed distally from the proximal end of the catheter to push the ball out of the socket in order to release the coil at the desired position. Such a system is disclosed in U.S. Pat. No. 5,350,397, entitled, "Axially Detachable Embolic Coil Assembly."

Another procedure for placing an embolic coil within a vessel is that of using a heat releasable adhesive bond for retaining the coil at the distal end of the catheter. One such system uses laser energy transmitted through a fiber optic cable to apply heat to the adhesive bond in order to release the coil from the end of the catheter. Such a procedure is disclosed in U.S. Pat. No. 5,108,407, entitled "Method and Apparatus for Placement of an Embolic Coil."

Yet another coil deployment system incorporates a catheter having a lumen throughout the length of the catheter and a distal tip for retaining the coil for positioning the coil at a preselected site. The distal tip of the catheter is formed of a material which exhibits the characteristic that when the lumen of the catheter is pressurized the distal tip expands radially to release the coil at the preselected site. Such a deployment system is disclosed in U.S. Pat. No. 6,113,622, entitled, "Embolic Coil Hydraulic Deployment System."

Still another coil deployment system incorporates an interlocking mechanism on the coil. The interlocking end on the embolic coil couples with a similar interlocking mechanism on a pusher assembly. A control wire which extends through the locking mechanism secures the coil to the pusher assembly. The pusher assembly and embolic coil are initially disposed within the lumen of a catheter. When the embolic coil is pushed out of the end of the catheter for placement, the control wire is retracted and the coil disengages from the pusher assembly. Such a deployment system is disclosed in U.S. Pat. No. 5,925,059, entitled, "Detachable Embolic Coil Assembly."

Yet another coil deployment system incorporates an embolic device detachably mounted on the distal portion of a pusher member and held in place with a connector thread or fiber. The fiber passes through a cutter member that may be activated to cut the connector fiber. Once the connector fiber is cut, the embolic device is released. Such a deployment system is disclosed in Published U.S. Patent Application No. 2002/0165569, entitled, "Intravascular Device Deployment Mechanism Incorporating Mechanical Detachment."

Still another coil deployment system incorporates an embolic device with a stretch resistant member therethrough. The distal end of the stretch resistant member attaches to the embolic coil and the proximal end of the stretch resistant member is detachably mounted on the pusher member through various means such as adhesive, or by a connector fiber adhered to or tied to the pusher member, and is detachable by the application of heat. Such a deployment system is disclosed in Published U.S. Patent Application No. 2004/0034363, entitled, "Stretch Resistant Therapeutic Device."

Still another coil deployment system incorporates a pusher wire with a stiff wavy-shaped end segment which is coupled to the embolic coil and is placed in the lumen of the catheter. The coil is advanced through the catheter until it reaches a predetermined site in the vessel at which time the pusher wire is retracted and the embolic coil is released. Such a system is disclosed in U.S. Pat. No. 6,203,547, entitled, "Vaso-occlusion Apparatus Having a Manipulable Mechanical Detachment Joint and a Method for Using the Apparatus."

A still further embolic device deployment system for placement of an embolic device, or coil, includes a delivery catheter and a flexible pusher member. The embolic device is retained by an interlocking mechanism which includes a detachment member which extends through an aperture in an engagement member. The engagement member engages a ring on the embolic device. When the detachment member is withdrawn from the aperture, the embolic device is released. One such deployment system is disclosed in Published U.S. Patent Application No. 2006/0276823, entitled, "Embolic Coil Delivery System with Mechanical Release Mechanism," and assigned to the same assignee as the present application.

SUMMARY

The present invention is directed toward a vascular occlusive embolic device deployment system for use in placing an embolic device at a predetermined site within a vessel which includes an elongated flexible catheter, an elongated pusher member having a lumen extending therethrough and being slidably disposed within the lumen of the catheter. The embolic device takes the form of an embolic coil defining a central lumen extending between the proximal and distal ends of the coil and having a retaining ring disposed on the proximal end of the coil. An engagement member, preferably having a generally L-shaped configuration, is fixedly attached to the distal end of the pusher member and includes an aperture extending through the distal end thereof. The engagement member extends through the retaining ring of the embolic device. The deployment system includes a kicker member which takes the form of an elongated projection which may or may not include an aperture extending therethrough, extending from the distal end of the pusher member and exhibits the characteristic of being normally biased parallel to the central axis of the lumen of the pusher member and is deflected in a direction which when it contacts the retaining ring will tend to cause the retaining ring of the embolic device to be lifted off of the engagement member. In addition, the deployment system includes an elongated detachment member which extends from the proximal end of the pusher member, through the lumen of the pusher member and through the aperture of the engagement member such that when the detachment member is pulled proximally the distal end of the detachment member is withdrawn from the aperture of the engagement member to thereby release the embolic device.

In accordance with another aspect of the present invention, the embolic device takes the form of an embolic coil having a fiber such as a platinum wire extending between the distal end of the coil and the retaining ring.

In accordance with another aspect of the present invention, there is provided a deployment system for use in placing an embolic device at a predetermined site within a vessel which includes an elongated flexible catheter, an elongated pusher member being slidably disposed within the lumen of the catheter. The embolic device takes the form of an embolic coil defining a central lumen extending between the proximal and distal ends of the coil. A stretch resistant member having first and second ends in which the first end of the stretch resistant member is attached to the distal section of the coil and the second end of the stretch resistant member is attached to a retaining ring. An engagement member, preferably having an L-shaped configuration, is fixedly attached to the distal end of the pusher member and includes an aperture extending through the distal end thereof. The engagement member extends through the retaining ring of the stretch-resistant embolic device. The deployment system includes a kicker member which takes the form of an elongated projection which may or may not include an aperture extending therethrough, extending from the distal end of the pusher member and exhibits the characteristic of being normally biased parallel to the central axis of the lumen of the pusher member and is deflected in a direction which when it contacts the retaining ring will tend to cause the retaining ring of the embolic device to be lifted off of the engagement member. In addition, the deployment system includes an elongated detachment member which extends from the proximal end of the catheter through the lumen of the catheter and through the aperture of the engagement member such that when the detachment member is pulled proximally the distal end of the detachment member is withdrawn from the aperture of the engagement member to thereby release the embolic device.

In accordance with another aspect of the present invention, the second end of the stretch-resistant member is attached to the proximal section of the coil, as opposed to the retaining ring, to prevent the coil from stretching, and the proximal end of the coil is attached to the retaining ring.

In accordance with another aspect of the present invention, the engagement member is of an L-shaped configuration and one of the legs is attached to the pusher member and the other leg extends through the retaining ring. The aperture of the engagement member extends through the leg which extends through the retaining ring such that when the detachment member extends through the retaining ring of the embolic device such that the embolic device is interlocked onto the engagement member until the detachment member is withdrawn from the aperture.

In accordance with another aspect of the present invention, the aperture of the retaining ring has a central axis which extends generally at a right angle to the central axis of the retaining ring. In addition, the embolic device takes the form of a helically wound embolic coil having a central axis which extends at a right angle to the central axis of the aperture of the retaining ring. The stretch resistant member is attached to and extends from a distal section to a proximal section of the helically wound coil.

In addition, the vascular embolic device deployment system preferably includes a retaining clamp mounted on the proximal end of the pusher member, and the detachment member extends from a position proximal of the retaining clamp and through a lumen in the clamp in order that the detachment member may be clamped in a fixed position prior to the release of the embolic device. Upon release of the clamp, the detachment member may be withdrawn from the aperture of the engagement member to thereby release the embolic device.

In accordance with another aspect or embodiment of the present invention, a deployment system for delivering an embolic device to a target location of a body vessel is provided. The deployment system includes an elongated flexible deployment catheter and an elongated pusher member slidably disposed within a lumen of the deployment catheter. An engagement member extends from the distal end of the pusher member and has an aperture extending through a distal end thereof. A portion of the engagement member extends through the retaining ring of an embolic device. Also extending from the distal end of the pusher member is a kicker member deflected in a direction toward a central axis of a lumen of the pusher member for engagement with the retaining ring. The kicker member is comprised of a shape memory material in a martensitic state at room temperature and automatically movable to a configuration substantially parallel to the central axis of the lumen of the pusher member at a transformation temperature greater than room temperature to lift the retaining ring of the embolic device off of the engagement member. An elongated detachment member extends from a position proximal to the proximal end of the pusher member, through the lumen of the pusher member and through the aperture of the engagement member such that when the detachment member is pulled proximally a distal end of the detachment member is withdrawn from the aperture of the engagement member and the kicker member lifts the retaining ring of the embolic device off of the engagement member to thereby release the embolic device from the pusher member.

According to another aspect or embodiment of the present invention, a method of connecting an embolic device to a deployment system is provided. The method includes a step of providing a tubular member comprised of a shape memory material and having a proximal end and a distal end. A kicker member and an engagement member are formed at the distal end of the tubular member and are substantially parallel to a central axis of the tubular member. An elongated pusher member is provided and secured to the proximal end of the tubular member. The engagement member and the kicker member are moved to a deflected configuration toward the central axis of the tubular member. An embolic device is provided and a retaining ring of the embolic device is positioned against the kicker member, with a portion of an aperture of the engagement member passing through the retaining ring. A detachment member passing through a lumen of the pusher member is passed through the aperture of the engagement member to releasably secure the embolic device to the pusher member.

According to another aspect or embodiment of the present invention, a component of a deployment system for delivering an embolic device to a target location of a body vessel is provided. The component includes an elongated pusher member and an engagement member extending from the distal end of the pusher member, with an aperture extending through a distal end of the engagement member. A kicker member is also provided, with a pair of arms extending away from the distal end of the pusher member in a direction away from a central axis of the lumen of the pusher member. A proximal crossbar extends between and connects distal ends of the arms. A pair of extensions are generally aligned with the arms and extend distally away from the proximal crossbar. The distal ends of the extensions are connected by a distal crossbar. The kicker member is movable toward the central axis of the lumen of the pusher member to a deflected configuration to cooperate with the engagement member to releasably secure an embolic device to the pusher member.

BRIEF DESCRIPTION OF THE DRAWINGS

FIGS. 3, 3A, 3B, and 3C are enlarged, sectional views of the coil deployment system shown in FIG. 1A illustrating the sequential steps in the advancement of the embolic device, removal of a detachment member, and release of the embolic device;

FIG. 4A is a side elevational view of a tubular member which may be incorporated into an embolic device deployment system;

FIG. 4B is a perspective view of the tubular member of FIG. 4A;

FIG. 5A is a side elevational view and 5B is a perspective view, each showing the tubular member of FIG. 4A with an engagement member thereof in a deflected configuration;

DESCRIPTION OF THE ILLUSTRATED EMBODIMENTS

Figure 1:
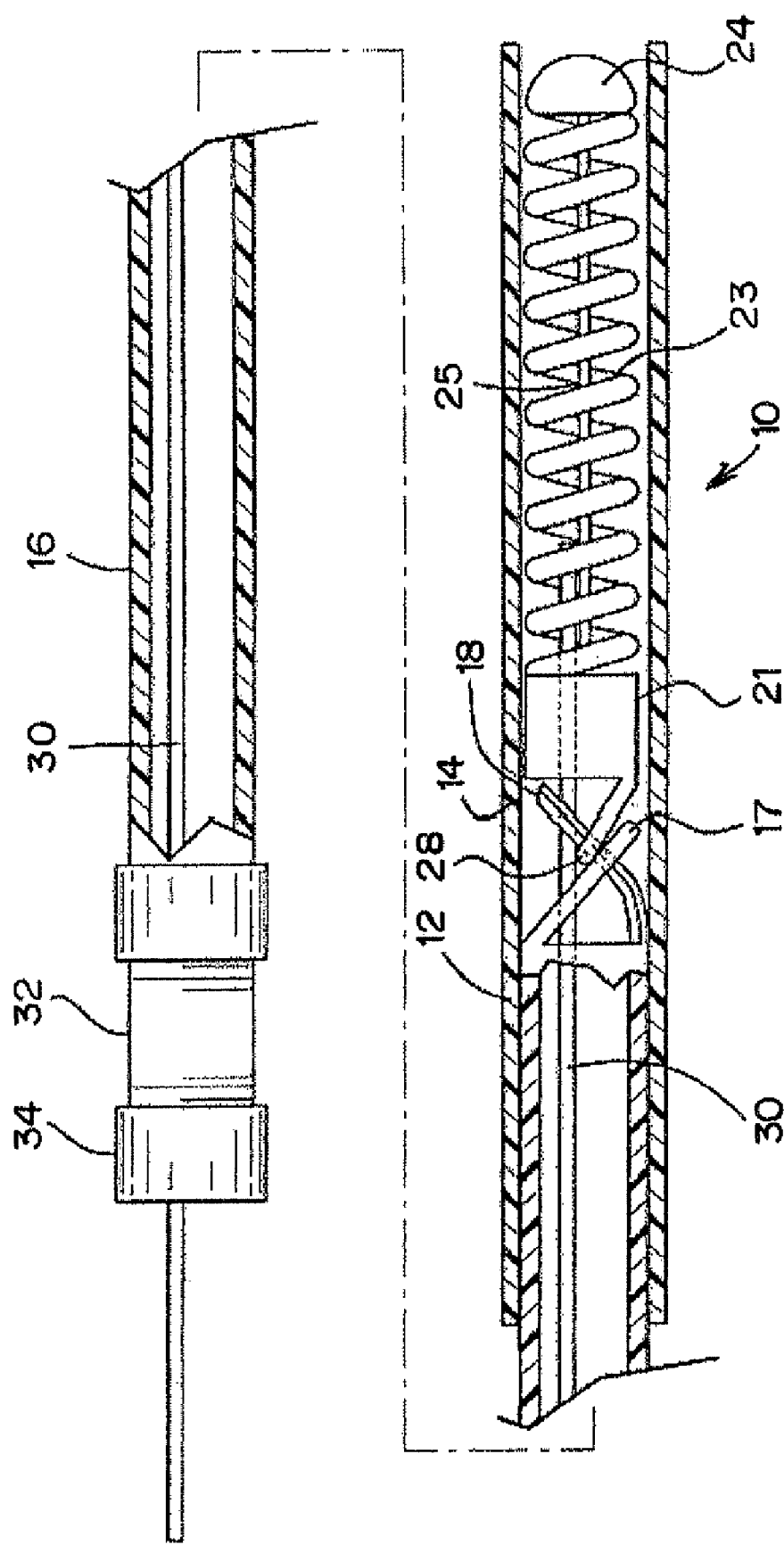
FIG. 1 is an enlarged, partially sectional view of an embodiment of an embolic device deployment system in accordance with the present invention.

FIG. 1 generally illustrates one embodiment of a vascular occlusive embolic device deployment system 10 which includes a sheath introducer 12 having a lumen 14 extending therethrough and having an elongated pusher member 16 slidably disposed within the lumen 14 of the sheath introducer 12. An elongated engagement member 18 extends distally from the pusher member 16 and has an aperture (to be described hereinafter) extending through the distal end thereof. The engagement member 18 is preferably formed from a distal section of the wall and of the pusher member 16 but may be formed as a separate member attached to the distal end of the pusher member 16.

The deployment system 10 also includes an embolic device 23, which as illustrated, preferably takes the form of a helically wound embolic coil, which is disposed in the distal section of the sheath introducer 12. While the embolic device as illustrated is shown as a helically wound coil various other types of embolic devices, such as filaments, braids, foams, expandable meshes and stents, could be delivered using the present deployment system and various other coil configurations could be delivered using this system. A weld, or solder, bead 24 is formed at the distal end of the embolic device 23 to provide an atraumatic tip for the embolic device. In addition, the distal end of a stretch-resistant member 25, which preferably takes the form of a platinum wire, is attached to the distal bead 24 and extends proximally through the central lumen of the coil. While the stretch-resistant member preferably takes the form of a platinum wire, other materials or composites such as polymers, metals and ceramics, having a low elongation relative to the coil elongation may also be suitable. Alternatively, the distal end of the stretch-resistant member could be attached to the coil at a more proximal location in the distal section of the coil. A headpiece 21 which takes the form of a cylindrical member is disposed on the proximal end of the embolic device 23. The headpiece 21 includes a retaining ring 28 which extends proximally from the cylindrical shaped headpiece. The proximal end of the stretch resistant member is then attached to the distal edge of the headpiece 21. Preferably, the retaining ring 28 has a central axis which extends at right angles to the central axis of the sheath introducer 12 and also extends at right angles to the central axis of the helically wound embolic coil.

Figure 1A:
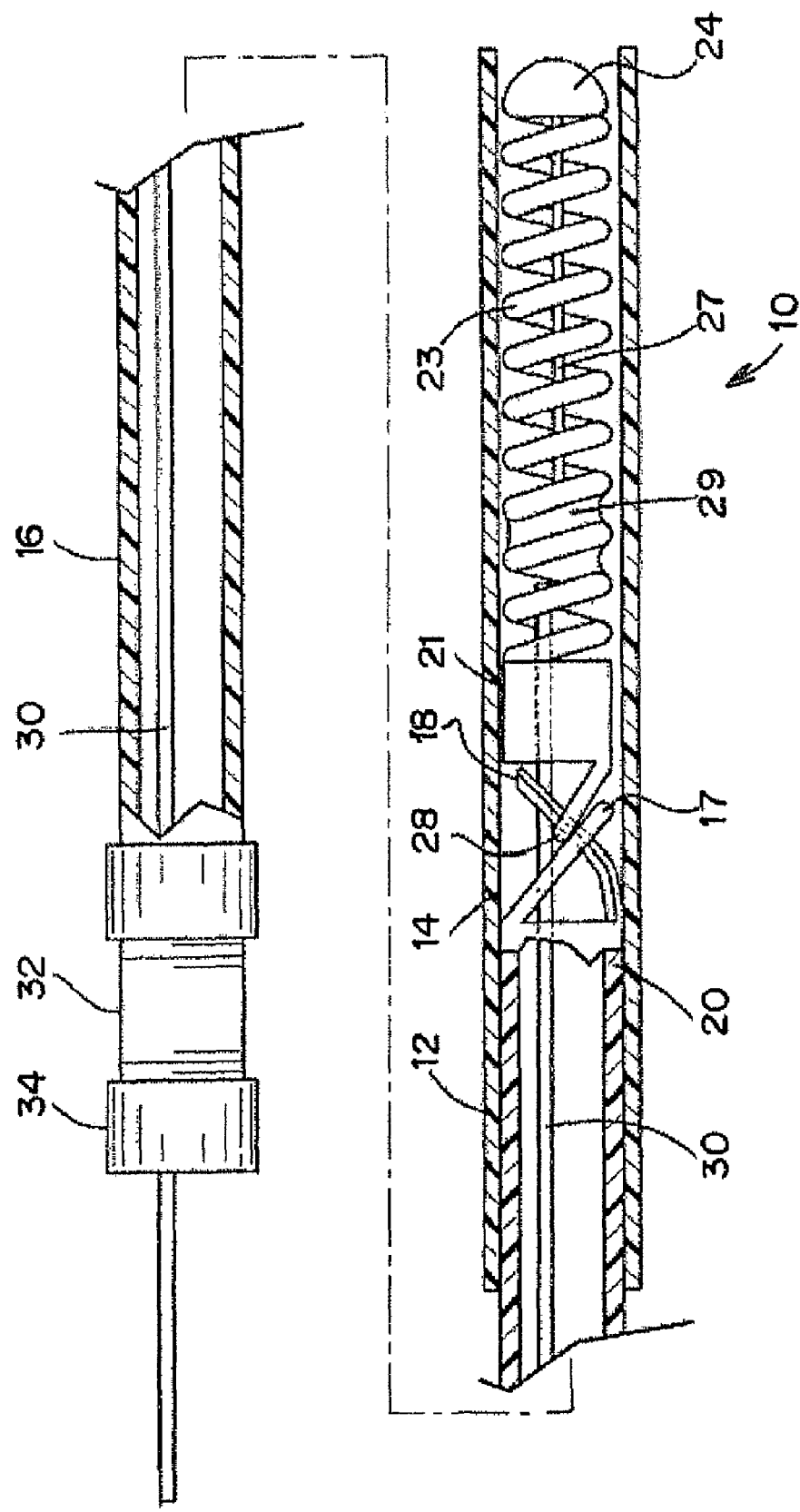
FIG. 1A is an enlarged, partially sectional view of a second embodiment of an embolic device deployment system in accordance with the present invention.

FIG. 1A illustrates another variation of the stretch-resistant embolic device 23 in which the distal end of a stretch-resistant member 27 is attached to the bead 24 at the distal end of the coil and the proximal end of the stretch-resistant member is attached to the turns in the proximal section of the coil by use of a weld, or solder, bead 29.

Figure 2A:
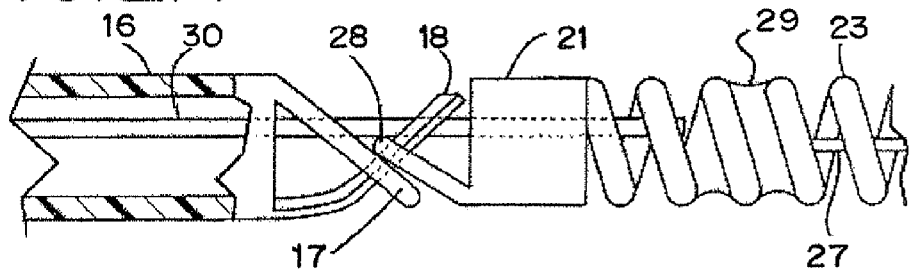
FIGS. 2A, 2B, 2C, and 2D are enlarged, sectional views, illustrating in more detail the coil deployment system of FIG. 1A.
Figure 2B:
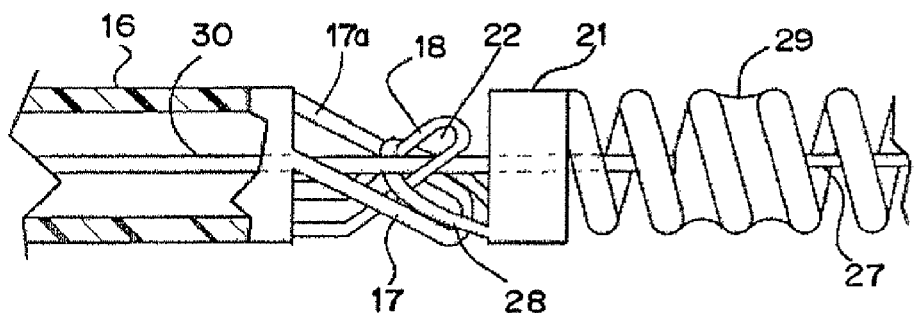

As illustrated in FIGS. 1, 1A, 2A and 2B, the engagement member 18 is of a generally L-shaped configuration and extends through the retaining ring 28. An elongated detachment member 30 extends from the proximal end of the deployment system 10 and through a lumen in the pusher member 16 and then through the aperture 22 (FIG. 2A) of the engagement member 18 and serves the function of interlocking the embolic device 23 to the pusher member 16 until such time as the detachment member 30 is withdrawn proximally. In order to improve the release mechanism an elongated kicker member 17 extends distally from the pusher member 16 and is preferably formed from a distal section of the wall of the pusher member, i.e., cut from the wall of the pusher member as an integral portion of the pusher member, but may also be formed as a separate member attached to the distal end of the pusher member. The kicker member 17 preferably has an aperture 17a which extends therethrough as shown in FIG. 2B. Alternatively, the kicker member 17 may be formed without an aperture. In such case, the kicker member takes the form of an elongated projection extending from the distal end of the pusher member 16. With this latter configuration the elongated kicker member may be formed from the wall of the pusher member or may be formed as a separate member attached to the distal end of the pusher member 16. The kicker member is normally biased in a direction parallel to the central axis of the lumen of the pusher member but is deflected from the wall of the pusher member in a direction toward the central axis of the lumen of the pusher member when the pusher member is engaged with embolic device 23. Also, the kicker member is normally biased in a direction which tends to lift the retaining ring 28 off of the engagement member 18 but is prevented from doing so unless the elongated detachment rod 30 is withdrawn from the aperture 22 of the engagement member 18.

The detachment member 30 preferably takes the form of a small diameter elongate filament, however, other forms such as wires or tubular structures are also suitable. While the detachment member 30 is preferably formed of nitinol, other metals and materials such as, stainless steel, PTFE, nylon, ceramic or glass fiber and composites may also be suitable.

A Tuohy-Borst type of clamp 32 is mounted on the proximal end of the pusher member 16 and when tightened onto the detachment member 30 serves to prevent movement of the detachment member until such time as the clamping cap 34 is loosened to release the grip onto this member.

FIGS. 2A and 2B illustrate the interlocking arrangement between the embolic device 23 and the pusher member 16 as shown in FIG. 1A, however, these figures illustrate the operation of the deployment system once the pusher member 16 has been moved distally to a position so that the distal end of the pusher member 16 extends slightly out of the distal end of the sheath introducer 12 or a delivery catheter thereby exposing the embolic device 23.

Figure 2C:
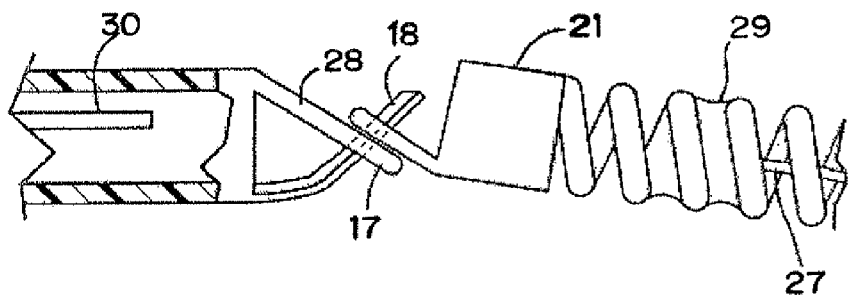
Figure 2D:
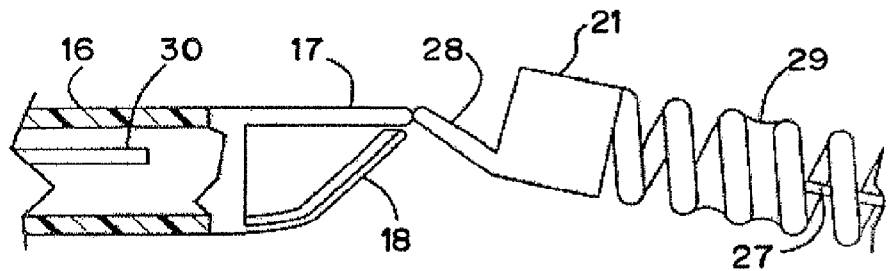

As illustrated in FIGS. 2C and 2D, once the embolic device 23 has been moved out of the end of the sheath introducer 12 the detachment member 30 may be pulled proximally to withdraw the detachment member from the aperture 22 of the engagement member 18 to thereby cause the engagement member to disengage from the retaining ring 28 of the embolic device thereby releasing the embolic device 23 at a preselected position. The kicker member 17 serves to ensure the release of the embolic device 23 by applying a force to the retaining ring 28 to lift the retaining ring 28 from the engagement member 18. Alternatively, if desired, the detachment sequence described above and illustrated in FIGS. 2A through 2D may be executed while the embolic device 23 is still within the lumen of sheath introducer 12 or a delivery catheter.

One of the important advantages of the present invention is that the embolic device may be placed at a desired location within a vessel, or within an aneurysm, with the configuration of the device deployment system as shown in FIGS. 2A and 2B. If it is determined that the embolic device is improperly positioned, the embolic device 23 may then be withdrawn from that location and placed at another location, or even removed from the body by first withdrawing the pusher member 16 and the embolic device totally back into the delivery catheter. Once the embolic device has been entirely withdrawn back into the delivery catheter, the catheter may then be moved to a more desirable location and the embolic device may then be released at the new location. With the addition of the stretch resistant member 27, the embolic device may be withdrawn without concern that the coil will stretch and become very difficult to remove.

Figure 3:
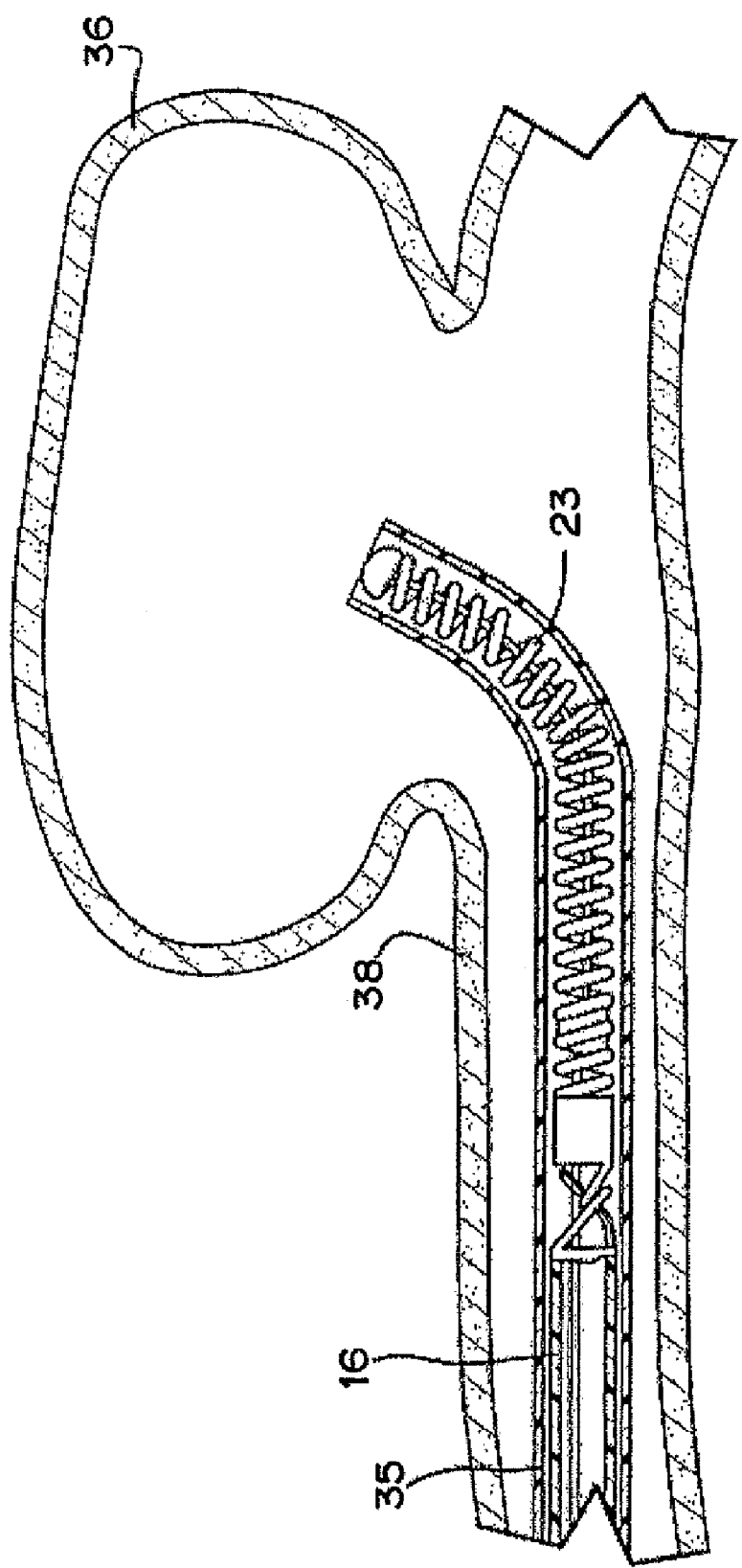
Figure 3B:
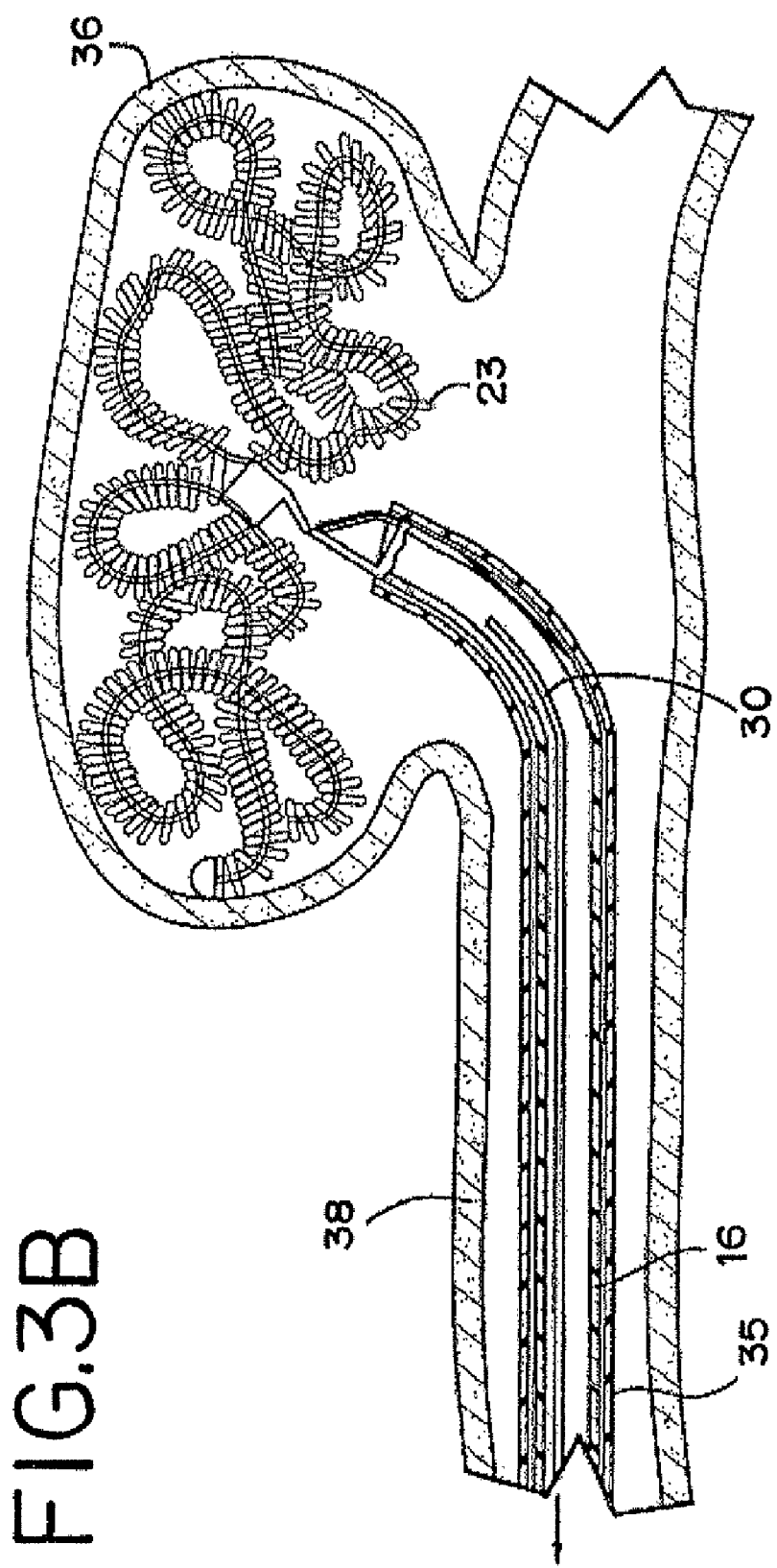

FIGS. 3, 3A and 3B generally illustrate the sequence of placing an embolic device, such as a helical wound coil into an aneurysm 36 which extends from a vessel wall 38. More particularly, FIG. 3 illustrates the vascular occlusive embolic device deployment system 10 in the same configuration as shown in FIG. 1A after the pusher member and associated embolic device have been inserted into a delivery catheter 35 and advanced into a position for deployment of the embolic device 23, shown as a helical embolic coil, into the aneurysm 36. FIG. 3A illustrates the deployment device having a configuration similar to FIG. 2A with the embolic device 23 being placed within the aneurysm 36 but prior to withdrawal of the detachment member 30. At this point, prior to the withdrawal of the detachment member 30, as previously mentioned, if it is determined that the embolic device has been improperly placed, the pusher member may be withdrawn thereby withdrawing the embolic device back into the delivery catheter 35 for repositioning to a different location, or alternatively, to remove the embolic coil entirely from the body.

FIG. 3B illustrates the deployment device after the detachment member 30 has been removed from the engagement member 18 thereby releasing the embolic device within the aneurysm 36, and FIG. 3C illustrates the deployment device after the pusher member 16 has been withdrawn back into the delivery catheter 35 at the completion of the procedure or alternatively in order to insert a second coil through the delivery catheter 35 and into the same aneurysm.

According to another embodiment of a deployment system of the present invention, the kicker member and/or the engagement member may be comprised of a material having shape memory properties. The kicker member, the engagement member, the embolic device, and the other components of the deployment system are otherwise provided in accordance with the foregoing description of the embodiments of FIGS. 1 to 3C, except as will be described herein. Deployment systems incorporating this aspect of the present invention will be described herein with reference to FIGS. 4A to 9.

Materials having shape memory properties are characterized by the ability to be deformed and thereafter automatically return to a default configuration upon application of an outside stimulus. It may be advantageous to provide a kicker member and/or an engagement member comprised of a heat-activated shape memory material, i.e., a material adapted to automatically return to a default configuration by application of heat.

Providing a kicker member and/or an engagement member comprised of a shape memory material may be achieved by any of a number of methods, such as by providing a hollow tubular member 100 comprised of a shape memory material. The tubular member 100 is shaped to form a kicker member 102 and an engagement member 104. The kicker member 102 and the engagement member 104 may be shaped by any of a number of methods, such as a laser cutting operation. The kicker member 102 and the engagement member 104 may take any of a number of forms, including the configuration described herein with regard to the embodiments of FIGS. 1 to 3C. In another embodiment, the kicker member 102 and the engagement member 104 may have the configuration illustrated in FIGS. 4A and 4B, which may be advantageous for reasons which will be described in greater detail herein. As shown in FIGS. 4A and 4B, the "as formed" or initial configuration of the kicker member 102 and the engagement member 104 has them extending substantially parallel to a central axis of the tubular member 100, which is typical if they are shaped by laser cutting the tubular member 100.

When the kicker member 102 and the engagement member 104 have been shaped, the tubular member 100 may be processed to impart particular performance characteristics to it. In particular, it may be advantageous to impart a preselected martensite-to-austenite transformation temperature to the shape memory material. The tubular member 100 may be treated to impart a martensite-to-austenite transformation temperature that is between room temperature and human body temperature, more advantageously being closer to human body temperature than room temperature, and most advantageously being slightly below human body temperature for reasons which will be described in greater detail herein. The various factors affecting the transformation temperatures of a shape memory material are well-known to those of ordinary skill in the art, and any of a number of procedures may be employed without departing from the scope of the present invention. Heat treatment is one method of processing a shape memory material and manufacturing, assembly, and deployment processes will be described herein with reference to a heat-activated shape memory material processed by a heat treatment operation, but the methods and apparatus described herein are merely illustrative.

Following the processing stage, the proximal end of the tubular member 100 is secured to the distal end of a pusher member 16, typically with the outer and inner diameters of the two being substantially the same and the central axes thereof being aligned with each other. The particular method of securing the tubular member 100 to the pusher member 16 may vary according to the nature of the shape memory material and the material composition of the pusher member 16. However, in one embodiment, the pusher member 16 is threaded at its distal end and the tubular member 100 has a mating thread at its proximal end and the two are joined by a rotational threading operation. A force fit approach also is available, typically accompanied by relative twisting motion between the pusher member and the tubular member.

It may be advantageous to employ an operation not involving the application of heat to avoid damaging the pusher member 16 and the tubular member 100 or possibly affecting the performance characteristics of the kicker member 102 and the engagement member 104. Such operations include the foregoing threading operation, a friction fit between the pusher member 16 and the tubular member 100, and a locking sleeve or shrink tube surrounding the interface between the pusher member 16 and the tubular member 100. However, heat-based methods, such as butt-welding the pusher member 16 to the tubular member 100 may also be employed without departing from the scope of the present invention.

Figure 6:
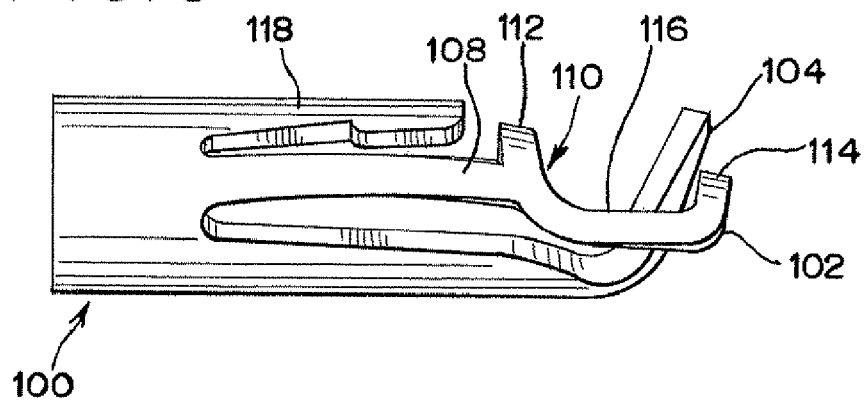
FIG. 6 is a side elevational of the tubular member of FIGS. 5A and 5B, with a kicker member thereof in a deflected condition.

With the tubular member 100 secured to the pusher member 16, the kicker member 102 and the engagement member 104 are typically subjected to a reshaping stage to bring them to the configuration of FIG. 6. To make the kicker member 102 and the engagement member 104 more workable, the temperature of the tubular member 100 may be reduced to bring it to a martensitic state, if not already at such a state during the foregoing joinder stage. It may be advantageous for the austenite-to-martensite transformation temperature of the tubular member 100 to be less than human body temperature and greater than room temperature or the temperature at which the deployment system is to be assembled. By such an arrangement, the kicker member 102 and the engagement member 104 are in a martensitic state during assembly and can be easily deformed to the deflected configuration of FIG. 6.

The engagement member 104 is reshaped by moving it to the deflected configuration of FIGS. 5A and 5B, at which the engagement member 104 is bent toward the common central axis of the tubular member 100 and the pusher member 16. This is typically a substantial deformation (a nearly 90° deformation in the embodiment of FIGS. 5A and 5B), which is generally sufficient to place the engagement member 104 in a state of plastic deformation which the shape memory property of the tubular member 100 cannot overcome, even at temperatures above the martensite-to-austenite transformation temperature. Hence, the engagement member 104 will remain in the deflected configuration of FIGS. 5A and 5B, performing substantially identically to the engagement member 18 of FIGS. 1 to 3C during use of the deployment system.

Figure 7:
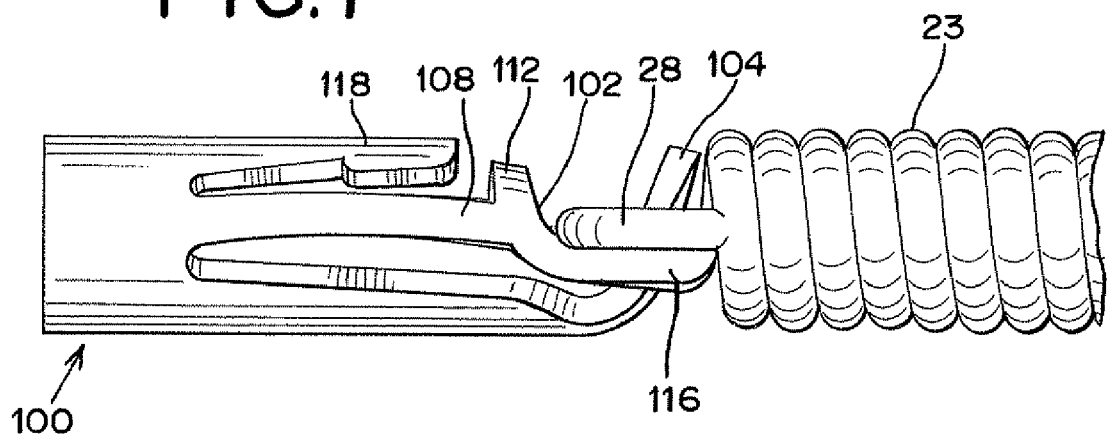
FIG. 7 is a side elevational view of the tubular member of FIG. 6, with an embolic device positioned on the kicker member.
Figure 8:
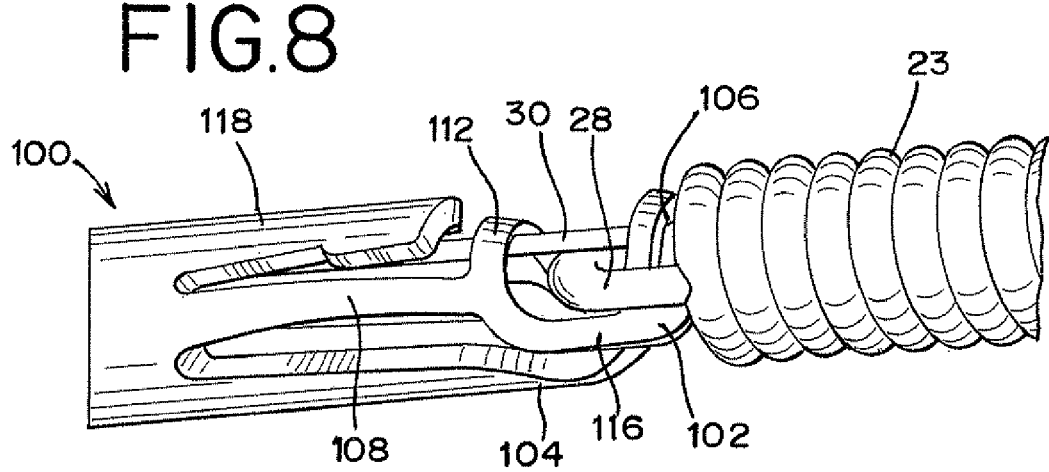
FIG. 8 is a perspective view of the tubular member of FIG. 7, with an embolic device secured thereto.

The kicker member 102 is reshaped by moving it to the deflected configuration of FIG. 6, in which the kicker member 102 is bent toward the common central axis of the tubular member 100 and the pusher member 16. This is a relatively minor deformation, which places the kicker member 102 in a state of elastic deformation which the shape memory property of the tubular member 100 can overcome at temperatures above the martensite-to-austenite transformation temperature. Moving the kicker member 102 to the deflected configuration of FIG. 6 is typically achieved by pressing on it with the retaining ring 28 of an embolic device 23, as shown in FIG. 7. With the kicker member 102, the engagement member 104, and the embolic device 23 in the configuration of FIG. 7, the detachment member 30 is passed through the aperture 106 of the engagement member 104 to releasably secure the embolic device 23 to the deployment system.

A deployment system incorporating at least a kicker member comprised of a shape memory material will operate generally according to the foregoing description of the embodiments of FIGS. 1 to 3C. However, rather than the kicker member 102 moving away from the engagement member 104 on account of its natural resiliency, it will more forcefully move away from the engagement member 104 due to its shape memory properties (provided that the martensite-to-austenite transformation temperature is less than human body temperature). This applies greater separation force to the embolic device 23 than is typically achieved by a kicker member comprised of stainless steel or another material not having shape memory properties.

In accordance with the foregoing description, it is advantageous to avoid moving the kicker member 102 to a state of plastic deformation during the reshaping stage. A number of steps may be taken to ensure that the kicker member 102 avoids plastic deformation as it is moved to the deflected configuration of FIG. 6. For example, in one embodiment, the tubular member 100 is comprised of a shape memory material also having super-elastic properties. As compared to a shape memory material not having super-elastic properties, this allows for a greater degree of recoverable deformation of the kicker member 102. Nickel-titanium alloys such as Nitinol are known to exhibit both shape memory and super-elastic properties, while being biocompatible, so it may be advantageous to provide the tubular member 100, or at least the kicker member 102, as a nickel-titanium alloy or nitinol material.

According to another method of avoiding plastic deformation of the kicker member 102, the kicker member 102 may include a pair of elongated arms 108, as shown in FIGS. 4A and 4B. The illustrated arms 108 are substantially identical, being tapered from a relatively thick section immediately adjacent to a solid portion of the tubular member 100 to a relatively thin portion immediately adjacent to an open saddle portion 110 of the kicker member 102. The illustrated arms 108 extend from the solid portion of the tubular member 100 from a position at or slightly above the vertical midpoint of the tubular member 100 (in the orientation of FIGS. 4A and 4B). The arms 108 are inclined upwardly toward the open saddle portion 100, i.e., away from the common central axis of the tubular member 100 and the pusher member 16, such that the arms 108 assume an arcuate configuration when the kicker member 102 is eventually moved to the deflected configuration of FIG. 6. It will be seen that the proximal and distal ends of the arms 108 are at substantially the same vertical elevation in the deflected configuration. It has been found that a kicker member 102 having the illustrated arms 108 may be moved to the deflected configuration while avoiding plastic deformation. Combining this feature with a super-elastic shape memory material further avoids the risk of plastically deforming the kicker member 102.

The kicker member 102 of FIGS. 4A and 4B is illustrated with an open saddle portion 110 at the distal end of the arms 108. The open saddle portion 110 is defined in part by a proximal crossbar 112 and a distal crossbar 114. The crossbars 112 and 114 are joined by a pair of arcuate extensions 116 generally aligned with the arms 108 (FIG. 4B). Such a configuration may be advantageous for a number of reasons. The kicker member 102 is relatively elongated, due in part to the arms 108, and the proximal crossbar 112 connects the distal ends of the arms 108 to each other to provide the kicker member 102 with improved strength and rigidity. This prevents the kicker member 102 from buckling as the pusher member 16 is moved through a body vessel or delivery catheter. To the extent that the kicker member 102 does begin to buckle during delivery of the embolic device 23, the proximal crossbar 112 will come into contact with an enlarged flange 118 of the tubular member 100, thereby preventing further buckling. Furthermore, in one embodiment, the proximal crossbar 112 is adapted to engage the detachment member 30 (FIG. 8), which further ensures that the detachment member 30 cannot deform or buckle and prematurely separate from the aperture 106 of the engagement member 104.

Figure 9:
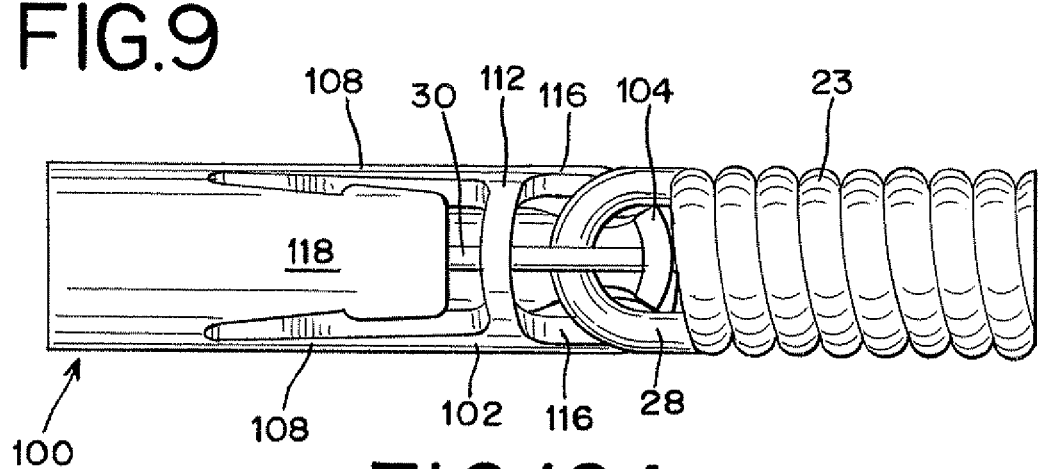
FIG. 9 is a top plan view of the tubular member and the embolic device of FIG. 8.

In accordance with the foregoing description, an enlarged flange 118 may extend from the tubular member 100 into the open space defined by the arms 108 and the proximal crossbar 112 (FIG. 9). In addition to contacting the proximal crossbar 112 upon buckling of the kicker member 102, the enlarged flange 118 provides the tubular member 100 with additional material, thereby improving its strength and substantially covering the area between the arms 108 to minimize the inflow of blood into the deployment system.

The kicker member configuration and the enlarged flange 118 illustrated in FIGS. 4A to 9 need not be limited to use with a tubular member or a kicker member comprised of a shape memory material, but may be formed of any material. For example, the kicker member configuration and enlarged flange 118 illustrated in FIGS. 4A to 9 may be incorporated into a pusher member 16 according to the foregoing description of the embodiments of FIGS. 1 to 3C, with the kicker member 102 and the enlarged flange 118 comprising shaped portions at the distal end of the pusher member 16.

A number of variations may be practiced with the tubular member 100 of FIGS. 4A to 9 without departing from the scope of the present invention. For example, radiopaque markers may be secured to the pusher member 16 or the tubular member 100 to assist in accurately positioning the embolic device 23 within a body vessel. It may be advantageous to provide one or more radiopaque markers on the engagement member 104 to provide visual feedback when the embolic device 23 has been released. Such radiopaque markers may be obscured by the retaining ring 28 of the embolic device 23 during delivery, such that they are only visible when the embolic device 23 has been released.

Figure 10A:
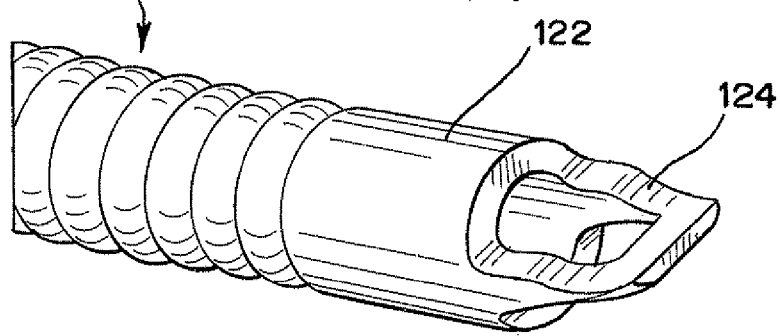
FIG. 10A is a perspective view of a proximal portion of an embolic device having an alternative embodiment of a headpiece suitable for use with the tubular member of FIGS. 4A to 9.
Figure 10B:
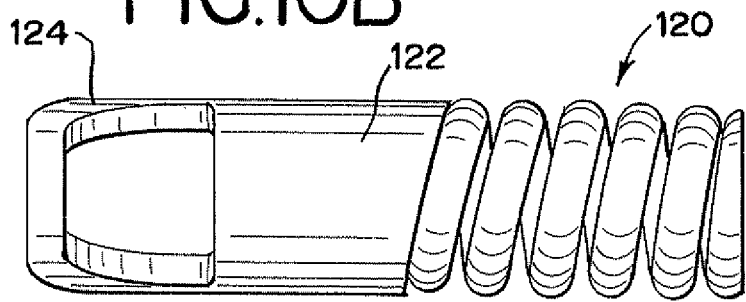
FIG. 10B is a top plan view of the embolic device portion of FIG. 10A.
Figure 10C:
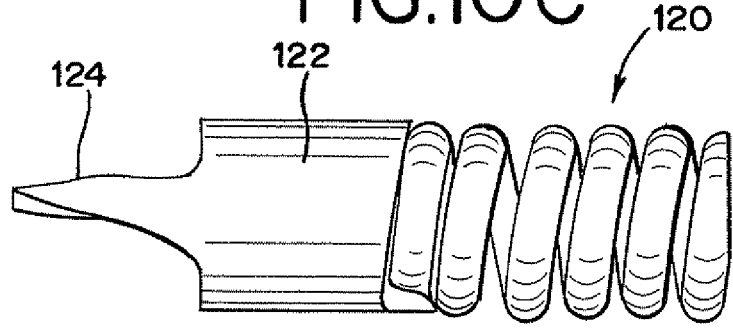
FIG. 10C is a side elevational view of the embolic device portion of FIG. 10A.

According to another embodiment, an embolic device 120 with a headpiece 122 (FIGS. 10A-10C) may be used in combination with the tubular member 100 of FIGS. 4A to 9, rather than providing the retaining ring as a coil aperture. The illustrated headpiece 122 has a retaining ring 124 with surfaces that are contoured to match the deflected configurations of the kicker member 102 and the engagement member 104, thereby providing a more secure fit.

As is apparent, there are numerous modifications of the preferred embodiment described above which will be readily apparent to one skilled in the art, such as many variations and modifications of the embolic device including numerous coil winding configurations, or alternatively other types of embolic devices. Also, there are many possible variations in the materials and configurations of the release mechanism. These modifications would be apparent to those having ordinary skill in the art to which this invention relates and are intended to be within the scope of the claims which follow.

The invention claimed is:

1. A deployment system for delivering an embolic device to a target location of a body vessel, comprising:
    an elongated flexible deployment catheter having a lumen extending therethrough and having proximal and distal ends;
    an elongated pusher member having a lumen extending therethrough and having proximal and distal ends and being slidably disposed within the lumen of the deployment catheter;
    an embolic device having a retaining ring at a proximal end thereof;

an engagement member extending from the distal end of the pusher member and having an aperture extending through a distal end thereof, a portion of said engagement member extending through said retaining ring;

a kicker member extending from the distal end of the pusher member, the kicker member being deflected in a direction toward a central axis of the lumen of the pusher member for engagement with said retaining ring of said embolic device, wherein said kicker member is comprised of a shape memory material in a martensitic state at room temperature and automatically movable to a configuration substantially parallel to the central axis of the lumen of the pusher member at a transformation temperature greater than room temperature to lift said retaining ring of said embolic device off of said engagement member; and an elongated detachment member extending from a position proximal to the proximal end of the pusher member, through the lumen of the pusher member and through the aperture of the engagement member such that when the detachment member is pulled proximally a distal end of the detachment member is withdrawn from the aperture of the engagement member and said kicker member lifts said retaining ring of said embolic device off of said engagement member to thereby release the embolic device from said pusher member.

2. The deployment system of claim 1, wherein said transformation temperature is between room temperature and human body temperature.

3. The deployment system of claim 1, wherein said kicker member is comprised of a material having shape memory and super-elastic properties.

4. The deployment system of claim 1, wherein said kicker member is comprised of a nickel-titanium alloy material.

5. The deployment system of claim 1, wherein said engagement member is comprised of a shape memory material.

6. The deployment system of claim 5, wherein said engagement member and said kicker member are comprised of the same shape memory material.

7. The deployment system of claim 1, further comprising a tubular member secured to the distal end of the pusher member and comprised of a shape memory material, wherein the kicker member and the engagement member are integrally formed at a distal end of said tubular member.

8. The deployment system of claim 1, wherein said kicker member comprises a pair of arms extending away from the distal end of the pusher member, a proximal crossbar extending between and connecting distal ends of the arms, a pair of extensions generally aligned with the arms and extending distally away from the proximal crossbar, and a distal crossbar extending between and connecting distal ends of the extensions.

9. A method of connecting an embolic device to a component of a deployment system, comprising:

providing a tubular member comprised of a shape memory material and having a proximal end and a distal end;

forming a kicker member at the distal end of the tubular member, wherein said kicker member is substantially parallel to a central axis of the tubular member;

forming an engagement member at the distal end of the tubular member, wherein said engagement member is substantially parallel to the central axis of the tubular member and defines an aperture;

providing an elongated pusher member having a lumen extending therethrough, a proximal end, and a distal end;

securing the proximal end of the tubular member to the distal end of the pusher member;

moving said engagement member to a deflected configuration toward the central axis of the tubular member;

moving said kicker member to a deflected configuration toward the central axis of the tubular member;

providing an embolic device having a retaining ring;

positioning the retaining ring of the embolic device against a portion of the kicker member, with a portion of the aperture of the engagement member extending through the retaining ring;

providing an elongated detachment member extending through the lumen of the pusher member; and passing a distal end of the detachment member through the aperture of the engagement member, thereby releasably securing the embolic device to the pusher member.

10. The method of claim 9, wherein said providing a tubular member includes providing a tubular member comprised of a shape memory material having a martensite-to-austenite transformation temperature between room temperature and human body temperature.

11. The method of claim 9, wherein said providing a tubular member includes providing a tubular member comprised of a material having shape memory and super-elastic properties.

12. The method of claim 9, wherein said providing a tubular member includes providing a tubular member comprised of a nitinol material.

13. The method of claim 9, wherein said providing a tubular member includes providing a tubular member having a kicker member comprising a pair of arms extending away from the distal end of the tubular member in a direction away from the central axis of the tubular member, a proximal crossbar extending between and connecting distal ends of the arms, a pair of extensions generally aligned with the arms and extending distally away from the proximal crossbar, and a distal crossbar extending between and connecting distal ends of the extensions.

14. The method of claim 9, wherein said moving said engagement member to a deflected condition includes plastically deforming the engagement member.

15. A component of a deployment system for delivering an embolic device to a target location of a body vessel, comprising:

an elongated pusher member having a lumen extending therethrough and having proximal and distal ends;

an engagement member extending from the distal end of the pusher member and having an aperture extending through a distal end thereof; and a kicker member comprising:
 a pair of arms extending away from the distal end of the pusher member in a direction away from a central axis of the lumen of the pusher member,
 a proximal crossbar extending between and connecting distal ends of the arms,
 a pair of extensions generally aligned with the arms and extending distally away from the proximal crossbar, and
 a distal crossbar extending between and connecting distal ends of the extensions,
 wherein the kicker member is movable toward the central axis of the lumen of the pusher member to a deflected configuration to cooperate with the engagement member to releasably secure an embolic device to the pusher member.

16. The component of claim 15, wherein said kicker member is comprised of a shape memory material.

17. The component of claim 15, wherein said kicker member is comprised of a material having shape memory and super-elastic properties.

18. The component of claim 15, wherein said kicker member is comprised of a nickel-titanium alloy material.

19. The component of claim 15, further comprising a tubular member secured to the distal end of the pusher member and comprised of a shape memory material, wherein the kicker member and the engagement member are integrally formed at a distal end of said tubular member.

20. The component of claim 15, further comprising an enlarged flange extending from the distal end of the pusher member to substantially decrease the amount of open space between the arms of the kicker member.

* * * * *